United States Patent [19]
Motloch

[11] Patent Number: 5,556,373
[45] Date of Patent: Sep. 17, 1996

[54] BODY-WORN ORTHOPEDIC DEVICE THAT INCLUDES INDIVIDUAL CONNECTED MODULES, AND A METHOD OF MANUFACTURING AND DESIGNING SUCH AN ORTHOPEDIC DEVICE

[76] Inventor: Wallace M. Motloch, 262 Beachview Ave., Unit #2, Pacifica, Calif. 94044

[21] Appl. No.: 271,750

[22] Filed: Jul. 7, 1994

Related U.S. Application Data

[62] Division of Ser. No. 945,413, Sep. 16, 1992, Pat. No. 5,344,390.

[51] Int. Cl.$^6$ ............................. A61F 5/00; A61B 19/00
[52] U.S. Cl. ................... 602/6; 128/898; 623/27
[58] Field of Search .................. 602/6, 7, 16, 20, 602/23–26, 28, 29; 623/23, 27, 28, 39, 46; 128/898

[56] References Cited

U.S. PATENT DOCUMENTS

| | | |
|---|---|---|
| 4,100,918 | 7/1978 | Glancy . |
| 4,494,534 | 1/1985 | Hutson . |
| 4,936,862 | 6/1990 | Walker et al. .......................... 623/23 |
| 5,054,476 | 10/1991 | Petrofsky et al. . |
| 5,121,747 | 6/1992 | Andrews . |

*Primary Examiner*—Linda C. Dvorak
*Attorney, Agent, or Firm*—Burns, Doane, Swecker & Mathis

[57] ABSTRACT

A body worn orthopedic device for use in improving poorly functioning parts of the body includes individual modules that are separately designed and fabricated to meet the needs and requirements of each part of the body that is affected. In the case of an orthopedic device for aiding in alignment of the upper and lower leg bones, the device can include a knee module comprised of a lower thigh engaging portion and a calf engaging portion. A separate and individual lower module is connected to the knee module and can be fabricated from materials that are different from the materials from which the knee module is fabricated. An upper module can also be connected to the knee module. The design of the orthopedic device begins at the knee module and works outwardly, thereby making it possible to design a superior orthopedic device.

10 Claims, 4 Drawing Sheets

BODY-WORN ORTHOPEDIC DEVICE THAT INCLUDES INDIVIDUAL CONNECTED MODULES, AND A METHOD OF MANUFACTURING AND DESIGNING SUCH AN ORTHOPEDIC DEVICE

This application is a divisional of application Ser. No. 07/945,413, filed Sept. 16, 1992, now U.S. Pat. No. 5,344,390.

FIELD OF THE INVENTION

The present invention pertains generally to an orthopedic appliance for use in improving poorly functioning parts of the body. More particularly, the present invention relates to a body-worn orthopedic device for facilitating a physically impaired individual's ability to stand or walk by the alignment of the upper portion of the individual's leg with the lower portion of the individual's leg.

BACKGROUND OF THE INVENTION

The ability to stand, walk, or otherwise support oneself in an upright position requires that the individual be capable of transmitting weight forces through his/her legs. This, in turn, requires that the individual be capable of straightening his/her legs so as to align the upper portion of the leg (i.e., the portion of the leg above the knee) with the lower portion of the leg (i.e., the portion of the leg below the knee). Unfortunately, some individuals are either unable to control physical movement of their legs or have very limited control of their legs, thereby making it quite arduous for these physically limited individuals to align the femur and tibia of the leg in the manner required for supporting the weight of the body. This physical handicap may be attributable to muscle weakness, muscle deterioration or damage, or a host of other problems. Whatever the cause, it is very difficult, if not impossible, for these physically handicapped individuals to stand, walk or otherwise support their weight while in an upright position without the use of some type of orthopedic aid.

Figure 1:
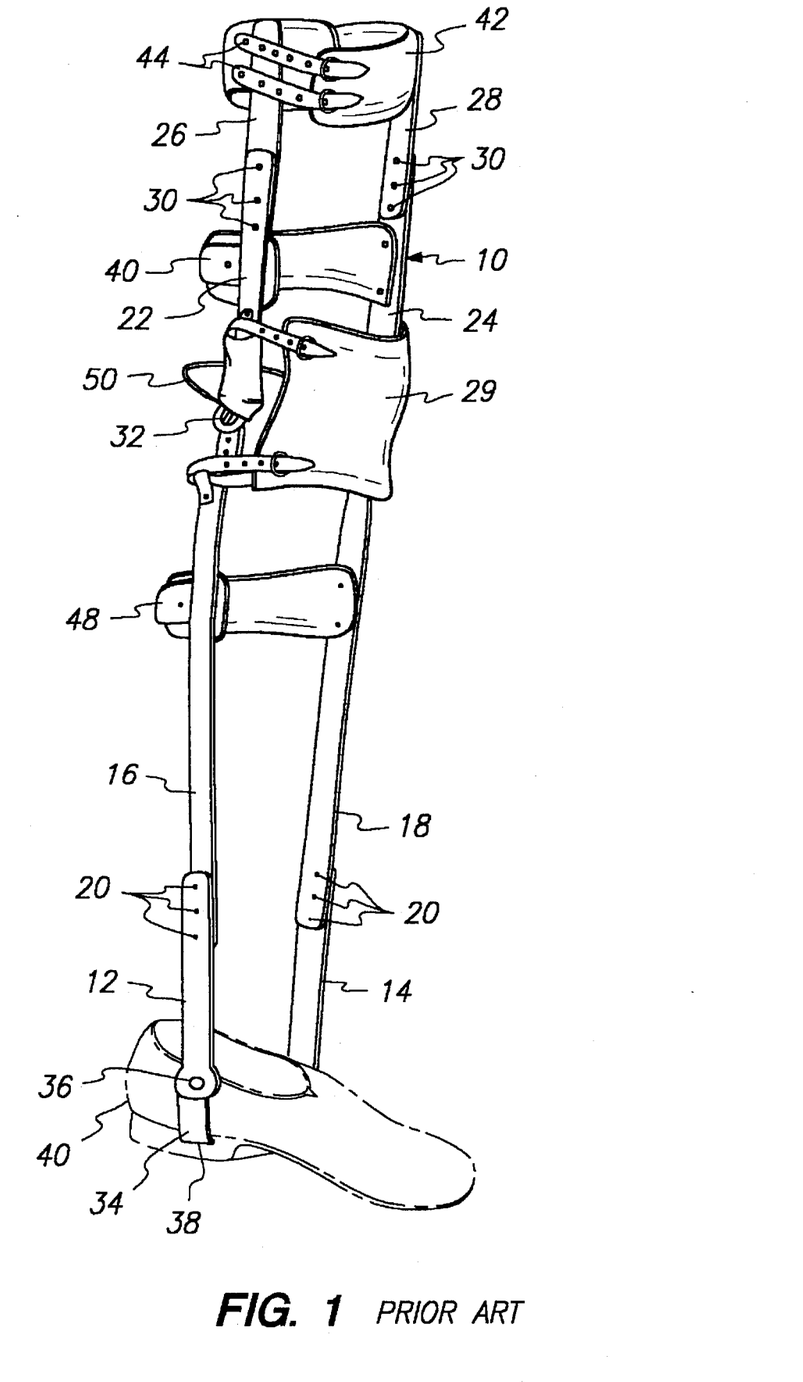
FIG. 1 is a perspective view of a known type of medical device.

FIG. 1 illustrates a typical known medical device worn by a physically handicapped individual in order to permit some amount of mobility and stability. As shown, the device 10 includes a pair of first lower rigid metal bars 12, 14 that are connected to a respective pair of second lower rigid metal bars 16, 18 by way of a suitable connecting arrangement such as rivets 20. A pair of first upper rigid metal bars 22, 24 are connected to a respective pair of second upper rigid metal bars 26, 28 by a suitable connecting arrangement such as rivets 30. The second lower rigid bars 16, 18 are connected to the first upper rigid bars 22, 24, respectively, by a joint connection 32 (only one of which can be seen in FIG. 1) that allows pivoting movement of the second lower bars 16, 18 relative to the first upper bars 22, 24.

The first lower rigid bars 12, 14 are connected to metal anchor stirrups 34 (only one of which can be seen in FIG. 1) by way of a joint 36 (only one of which can be seen in FIG. 1). The anchor stirrups 34 are secured in slots 38 provided in the heel portion of a shoe 40. The joint 36 allows pivoting movement of the individual's ankle during use.

The device 10 also includes a padded tongue 42 that is secured to the pair of second upper rigid bars 26, 28 for tightening against the upper thigh of the individual. Adjustable straps 44 permit the tongue 42 to be tightened. A thigh band 46 is also provided for resting against the rear part of the upper leg portions. The lower portion of the leg rests against shin band 48. Knee cap 29 is included to rest against the individual's patella.

In order to lock the metal bars 16, 22 and 18, 24 in a vertical position (i.e., in the position shown in FIG. 1), a known locking mechanism is provided. A releasing lever 50 unlocks the locking mechanism to allow the second lower bars 16, 18 to pivot relative to the first upper bars 22, 24, thereby allowing the individual to bend his/her leg at the knee.

Medical devices of the type illustrated in FIG. 1 are typically designed to support and transfer at least a portion of the individual's body weight through the rigid metal bars 26, 28, 22, 24, 16, 18, 12, 14 and to the shoe 40. In fact, some of these devices are specifically designed to fit under the ischial tuberosity in the pelvic region so that in essence, the individual "sits" on the orthopedic device, thereby transmitting his/her body weight through the rigid metal bars 26, 28, 22, 24, 16, 18, 12, 14 and to the shoe 40. Thus, in addition to aligning the upper and lower leg portions of the individual, these devices actually serve to support a significant amount of the individual's weight.

It can be readily appreciated that devices such as those shown in FIG. 1 suffer from certain disadvantages and drawbacks. For example, the devices are quite heavy, thereby making it difficult for the individual to walk. The devices can also be cumbersome and difficult to use and care for.

The devices also suffer from the drawback that they are designed from the shoe or foot upwards, much like one would construct a building from the foundation upward. Beginning at the shoe 40, the technician or designer simply connects together the rigid metal bars of appropriate length to result in a device that is suitably sized to fit the individual. The disadvantage with this type of construction is that the materials and characteristics needed at the knee joint, for example, can differ significantly from the materials and characteristics that are needed at other portions of the leg, for example, the ankle and foot. Moreover, little attention is paid to ensuring that the device possesses sufficient rigidity in the knee area.

Known orthopedic devices of the type illustrated in FIG. 1 are also not well-suited for resisting torsional forces. That is due, at least in part, to the fact that the devices are designed with two metal bars extending along opposite sides of the leg. The inadequate nature of the devices in this regard can cause misalignment of the bones at the joints and, consequently, undesirable wear.

Another problem associated with known devices such as the one illustrated in FIG. 1 is that the rigid metal bars do not permit a relatively close contact fit with the body, particularly in the area of the knee and on either side of the knee region. As a result, an undesirable amount of "play" or motion is permitted in the axial direction (i.e., along the length of the leg). This can cause the ligaments in the knee area to become over-stretched, thereby adding to the individual's physical impairment.

Further, as noted above, the known types of devices are often designed so that the device itself actually supports a significant amount of the individual's weight. Because the load is not transferred directly through and supported by the bones and joints, there may be a tendency for the bones to atrophy. Also, because the devices are sometimes designed to contact the ischial tuberosity in the pelvic region, the skin or tissue in that area can become bruised, and sores can result.

SUMMARY OF THE INVENTION

To address and overcome at least the foregoing disadvantages and drawbacks, the present invention provides a body-worn orthopedic device that includes individual modules connected to one another which result in an orthopedic device that is well-suited to which needs and characteristics of an individual. The orthopedic device is designed and constructed beginning in the region of a joint, for example the knee, and working outwardly.

In accordance with one aspect of the present invention there is provided, a body-worn orthopedic device for use by a physically impaired individual to aid in the alignment of bones on either side of a joint, comprising: a base module for supporting a joint of an individual, the base module including a first shell section for closely contacting a portion of the individual's body on one side of the joint, a second shell section for closely contacting a portion of the individual's body on an opposite side of the joint, and means connecting the first and second shell sections to one another for permitting movement of the first and second shell sections relative to one another; and another module connected to said base module, said another module including a third shell section for closely contacting a portion of the individual's body positioned on one side of the joint and distally from the joint, said third shell section being fabricated from a composition of material that is different from the composition of material from which the first and second shell sections are fabricated.

In accordance with the preferred embodiment of the present invention, the hinge means can include means for locking the first shell section in a position relative to the second shell section such that the portions of the individual's body on either side of the joint are in substantial axial alignment. Additionally, the first and second shell sections have greater rigidity than the third shell section and the third shell section can be fabricated to be more flexible than the first and second shell sections.

In accordance with another aspect of the present invention there is provided, a body-worn orthopedic device for use by a physically impaired individual to aid in alignment of an individual's tibia and femur, comprising: a knee module adapted to be mounted on an individual's knee as well as portions of the individual's leg positioned above and below the knee, said knee module including a lower thigh engaging portion for engaging a portion of the individual's leg positioned above the knee, a calf engaging portion for engaging a portion of the individual's leg positioned below the knee, and hinge means connecting the lower thigh engaging portion to the calf engaging portion and for permitting movement of the calf engaging portion relative to the lower thigh engaging portion, said hinge means including means for locking the calf engaging portion in a position relative to the lower thigh engaging portion such that the calf engaging portion is substantially axially aligned with the lower thigh engaging portion and such that the individual's tibia and femur are substantially axially aligned with one another.

In a preferred embodiment, the device can also include means for releasing the locking means so that the calf engaging portion and the lower thigh engaging portion can be selectively locked in place relative to one another and released for relative movement. Additionally, the device can include a lower module connected to the knee module for engaging the lower leg and foot of the individual. The lower module is preferably substantially L-shaped and is fabricated from a composition of material that is different from the composition of material from which the lower thigh engaging portion and the calf engaging portion are fabricated. The device can also include an upper module that is connected to the lower thigh engaging portion of the knee module for engaging an upper portion of the individual's thigh.

In accordance with an additional aspect of the present invention there is provided, a method of manufacturing a body-worn orthopedic device for use by a physically impaired individual to aid in alignment of the individual's tibia and femur, comprising the steps of: fabricating a knee module for being positioned on an individual's knee as well as portions of the individual's leg located above and below the knee, said steps of fabricating the knee module including: determining the dimensions and configuration of the individual's lower thigh, fabricating a lower thigh engaging portion to closely contact the individual's lower thigh based upon the determined dimensions and configuration of the individual's lower thigh; determining the dimensions and configuration of the individual's calf; fabricating a calf engaging portion to closely contact the individual's calf based upon the determined dimensions and configuration of the individual's calf connecting the lower thigh engaging portion to the calf engaging portion by a hinge means that permits movement of the calf engaging portion relative to the lower thigh engaging portion; and providing said hinge means with locking means for permitting said calf engaging portion to be locked in a substantially axially aligned position with respect to said lower thigh engaging portion.

In accordance with a preferred embodiment of the method according to the present invention, the method can involve the fabrication of a lower module for engaging the individual's lower leg and foot, and connecting the lower module to the calf engaging portion of the knee module after fabrication of the knee module. The lower module can be fabricated from a composition of material that is different from the composition of material from which the lower thigh engaging portion and the calf engaging portion are fabricated. An additional step in the preferred embodiment of the method can include fabricating an upper module for engaging the individual's upper thigh, and connecting the upper module to the upper thigh engaging portion of the knee module after fabrication of the knee module.

In still another aspect of the present invention there is provided, a method of designing a body-worn orthopedic device for use by a physically impaired individual to aid in the functioning of a limb of the individual's body that includes a joint, said device including a base module and another module connected to the base module, the method comprising the steps of: first analyzing the joint of the individual to determine the stresses and forces to which the joint is subjected; designing a base module to be worn by the individual in the area of the joint, said step of designing the base module including designing a first section for closely contacting a portion of the individual's body on one side of the joint, a second section for closely contacting a portion of the individual's body on an opposite side of the joint, and a connecting section for connecting the first and second sections and for permitting movement of the joint, said first section, said second section and said connecting section being designed to result in a base module that possesses characteristics necessary for withstanding the stresses and forces to which the joint is subjected; analyzing the portion of the limb of the individual remote from the joint to determine the stresses and forces to which said portion of the limb is subjected; and designing a lower module that is to be connected closely to contact said portion of the limb, said lower module being designed to result in a lower module that possesses characteristics necessary for withstanding the stresses and forces to which said portion of the limb is subjected.

In the preferred embodiment of the method, the first and second sections can be designed to be fabricated of a composition of material that is different from the composition of material from which the lower module is designed to be fabricated. The design of the connecting section can include locking means for locking the second section relative to the first section in an axially aligned manner.

BRIEF DESCRIPTION OF THE DRAWING FIGURES

The features of the present invention will become apparent from the description that follows considered in conjunction with the drawing figures in which like elements bear like reference numerals and wherein.

DETAILED DESCRIPTION OF THE PRESENT INVENTION

Figure 2:
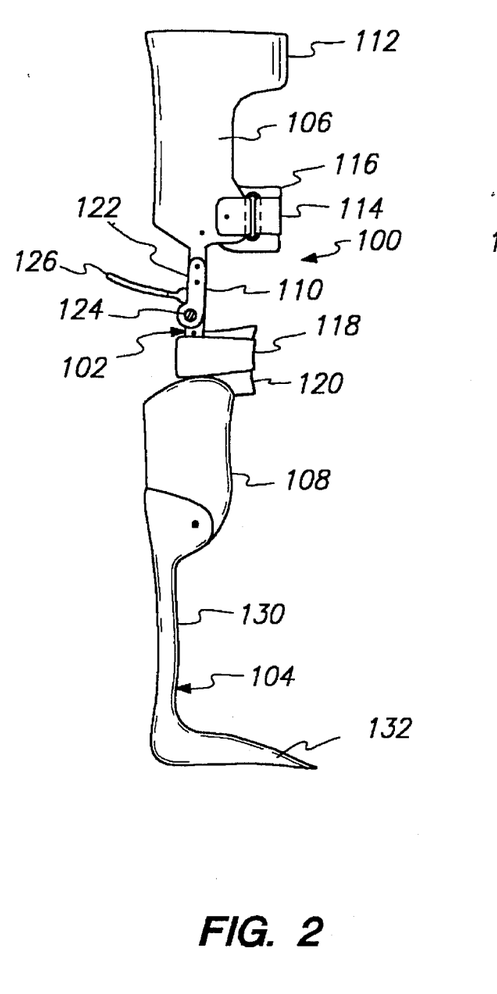
FIG. 2 is a side view of the orthopedic device according to one embodiment of the present invention.
Figure 3:
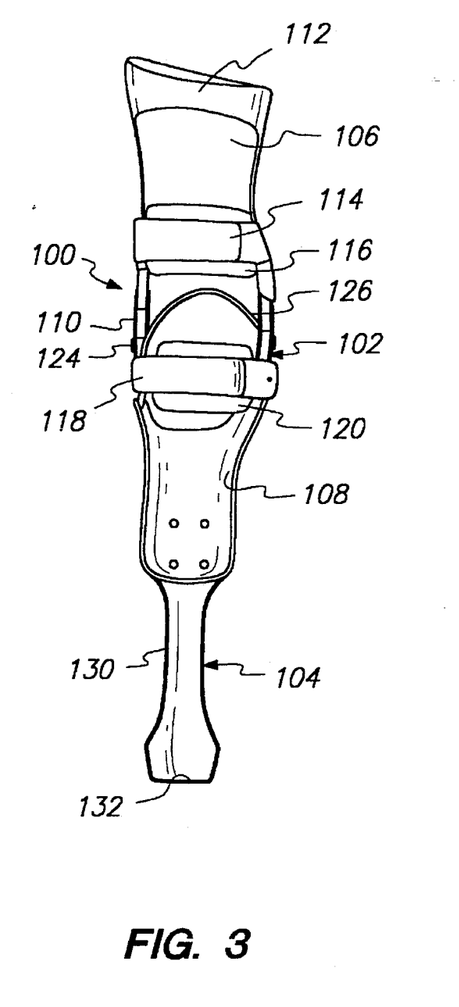
FIG. 3 is a frontal view of the orthopedic device showing in FIG. 2.
Figure 4:
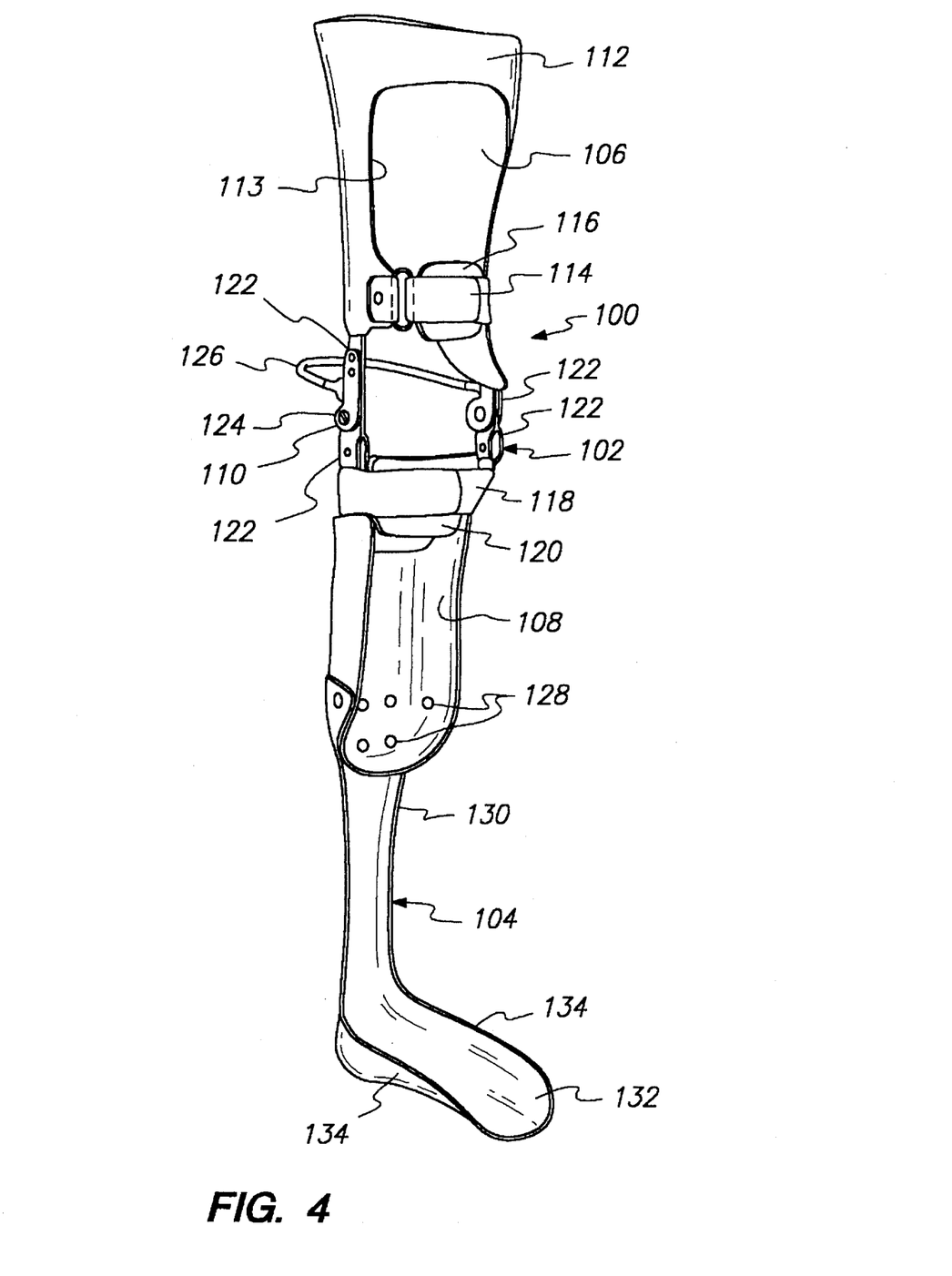
FIG. 4 is a perspective view of the orthopedic device shown in FIG. 2.

With reference initially to FIGS. 2–4, one embodiment of the orthopedic device shown generally at 100 according to the present invention will be described. For reasons that will become apparent from the description below, the orthopedic device according to the present invention is fabricated from several individual modules that are connected to one another to define the orthosis. Moreover, the orthopedic device 100 is designed beginning at the knee region and working outwardly.

In accordance with one embodiment, the orthopedic device 100 includes a base module or knee module 102 and a lower module or lower leg/foot module 104. The knee module 102 is generally comprised of three sections: a first section or lower thigh engaging portion 106, a second section or calf engaging portion 108, and a connecting arrangement 110 for connecting the lower thigh engaging portion 106 to the calf engaging portion 108.

The lower thigh engaging portion 106 is a generally C-shaped shell section that is adapted to closely contact and encircle the portion of an individual's leg positioned above the knee. The upper part 112 of the lower thigh engaging portion 106 is adapted to completely surround and encompass the individual's leg while the remaining part 113 of the lower thigh engaging portion 106 is open at the front. Thus, the lower thigh engaging portion 106 is essentially a cylindrical member that is provided with the opening in remaining part 113 along one portion. An adjustable strap 114 that is provided with suitable padding 116 extends across the open front area of remaining part 113 of the lower thigh engaging portion 106 to help firmly secure the lower thigh engaging portion 106 to the lower thigh of the individual.

The calf engaging portion 108 is generally U-shaped so as to engage the back portion of the individual's leg positioned below the knee (i.e., the calf). At the upper end of the calf engaging portion 108, or just above the upper end of the calf engaging portion 108, an adjustable strap 118 having a pad 120 secured thereto is provided to closely fit against the front part of the individual's lower knee.

The connecting arrangement 110 for connecting the lower thigh engaging portion 106 to the calf engaging portion 108 can include the four metal bars 122 that extend from opposite sides of the lower thigh engaging portion 106 and the calf engaging portion 108. These metal bars 122 meet at a hinge means 124 that permits the calf engaging portion 108 and the attached metal bars 122 to pivot relative to the lower thigh engaging portion 106 and the metal bars 122 extending therefrom.

Since the orthopedic device 100 according to the embodiment of the present invention shown in FIGS. 2–4 is adapted to aid in alignment of an individual's tibia and femur for purposes of facilitating standing and walking, the hinge means 124 is provided with a suitable arrangement for locking the calf engaging portion 108 in a substantially axially aligned position with respect to the lower thigh engaging portion 106. Known mechanisms for achieving this objective include a bale lock, a ring lock, a drop lock, etc. Such known mechanisms, or any other type of mechanism for achieving the same objective, can be employed. In view of their known characteristics, those locking mechanisms are not described in detail here.

The orthopedic device 100 is also provided with a release mechanism or lever 126 that releases the aforementioned locking mechanism so as to permit the calf engaging portion 108 to pivot relative to the lower thigh engaging portion 106, as desired. Releasing mechanisms of this type are also known and need not be described in detail here.

The lower module or lower leg/foot module 104 is secured to the calf engaging portion 108 by any suitable means such as rivets 128. The lower module 104 is substantially L-shaped and includes a generally vertically extending portion 130 and a generally horizontally extending portion 132. The vertically extending portion 130 is adapted to extend along the back side of the individual's lower leg to the heel, while the horizontally extending portion 132 is adapted to be positioned under the individual's foot. For that reason, the horizontally extending portion 132 can be provided with upturned sides 134 that extend upwardly along the sides of the individual's foot. The lower module 104 is preferably designed such that the horizontal by extending portion 132 can be positioned in the individual's shoe with the individual's foot resting on top of the horizontally extending portion 132.

As can be seen from FIG. 3, the orthopedic device 100 according to the present invention is substantially symmetrical about a vertical median plane extending the length of the device 100. Of course, the orthopedic device 100 need not be symmetrical, but can, if desired, be specifically adapted to suit the particular needs of an individual.

The orthopedic device or orthosis 100 according to the present invention differs from other known leg braces in several respects. A significant difference resides in the fact that the design and construction of the orthosis 100 according to the present invention begins at the knee area and works outwardly away from the knee region (i.e., down the leg to the foot, and possibly up the leg to the hip and pelvic region).

The knee joint in human beings develops some of the greatest bending forces and is prone to many deformities and injuries. If the ligaments, connective tissues, or musculature is defective, an orthopedic brace or orthosis can be used to protect, align and otherwise aid in stabilizing the defective condition. It follows, therefore, that some of the greatest forces and stresses to which the brace is subjected also occur in the knee region. It is the knee portion of the orthopedic device or orthosis, therefore, that requires the maximum strength, rigidity and durability. Further, it is this knee portion of the orthosis in which the fit of the orthosis should preferably be most intimate and closely contacting with the individual's body in order to provide sufficient support to transmit external forces to the skeleton of the body. The orthosis should preferably be designed to cause the least interference with clothing, and it should be capable of aligning the bones of the thigh and the bones of the shin to achieve sufficient weight-bearing alignment of those bones.

Given the significance and importance of the knee region of orthopedic devices, the design and fabrication of the orthosis 100 according to the present invention begins at the knee and works outwardly towards the foot and, when desired, outwardly towards the hip and pelvic region. This method of designing and fabricating orthopedic devices lends itself quite readily to creating a superior knee cage as a base module of the bracing system. By selectively adding to that base module a lower leg/foot module, and possibly an upper thigh/pelvic region module, to achieve certain characteristics, it is possible to create a specifically designed support system for each individual to achieve particularly desired results. This modular approach to designing and constructing the orthopedic device allows each module to be fabricated of superior design and materials in dependence upon the functional characteristics of each module. This modular approach also permits each of the modules to be closely fitted to the particular needs of an individual.

The modular construction of the orthosis 100 is superior to prior known devices because it makes it possible to take into account the specific forces, stresses and conditions to which each of the various parts of the orthopedic device is subjected during use. For example, in the case of an orthosis 100, such as shown in FIGS. 2–4, for aligning the shin bones and thigh bones to support a load through the skeletal system of the individual, the materials and characteristics needed at the knee joint must be sufficient to withstand torsional or twisting forces, shear forces, and side-to-side forces that predominately affect the knee area. Thus, the materials and functional characteristics of the orthosis in the area of the knee joint require a very rigid and strong module.

In contrast, the lower leg/foot region experiences predominately front-to-back flexure and a small amount of longitudinal twist. Thus, in this area of the orthopedic device, it is much more desirable to employ a flexible module that allows the foot to flex relative to the lower leg and ankle. The modular construction permits one set of characteristics to be emphasized in the knee area of the orthosis and another set of completely different characteristics to be emphasized at the lower leg/foot area of the orthosis.

In accordance with a preferred embodiment of the orthosis shown in FIGS. 2–4, the lower thigh engaging portion 106 and the calf engaging portion 108 are fabricated from a composition of material for producing the requisite strength and rigidity. The composition of material can include the combination of plastic material and reinforcing fibers. The reinforcing fibers can be high modulus fibers in the form of carbon fibers, graphite fibers, or a mixture of both.

The lower module 104, on the other hand, can be fabricated from plastic material that is devoid of reinforcing fibers. This results in a lower module 104 that is much more flexible than the calf engaging portion 108 and the lower thigh engaging portion 106, and indeed the knee module 102 as a whole. The calf engaging portion 108 and the lower thigh engaging portion 106, the knee module 102 as a whole, preferably have greater rigidity than the lower module 104. The plastic material can be any suitable plastic material, such as polypropylene, that is capable of providing the desired flexibility.

The metal bars which interconnect the lower thigh engaging portion 106 and the calf engaging portion 108 can be made of stainless steel or titanium or aluminum. Preferably, the metal bars 122 are molded directly into the calf engaging portion 108 and the lower thigh engaging portion 106. This results in a very strong and very rigid connection that is able to maintain its strength and rigidity even after repeated loading and unloading over extended periods of time. In typical known orthopedic devices, a significant amount of "play" oftentimes develops in the knee area of the device, even after only short periods of use. This "play" in the knee area can detrimentally affect the proper alignment of the shin bones and the thigh bones, thereby adding to the individual's impairment. The very strong and rigid connection that results from molding the metal bars 122 of the orthosis 100 according to the present invention directly into the laminates of the lower thigh engaging portion 106 and the calf engaging portion 108 significantly reduces the amount of "play" that occurs in the knee area. Consequently, misalignment of the hinge means 124 is not as problematic as with other known orthopedic devices. The subject invention ensures that the brace locks and unlocks properly and that the joint wear is minimal.

The modular nature of the orthopedic device 100 according to the present invention can also provide certain advantages during the manufacturing process. Since the knee module is quite an important feature of the overall orthosis 100, insofar as strength and rigidity is concerned, and the types of materials required to achieve those characteristics, it may be desirable in certain instances to manufacture the knee module at a specific facility having highly skilled orthotists and technicians. These highly skilled individuals could aid in the design of the componentry of the knee module and could employ unique manufacturing equipment and processes that might not otherwise be available or affordable to a local orthotics facility. A local orthotics facility would not need to be as specialized and could, therefore, employ less expensive personnel and equipment.

On the other hand, the lower module 104 is much better suited to manufacture by a local orthotics facility since it does not necessarily require expensive equipment or highly trained personnel. Thus, as a result of the modular construction of the orthosis 100, it is possible to have the more complex parts of the orthopedic device manufactured by an outside facility while still permitting the manufacture of certain parts of the orthosis at a local facility.

To fabricate the orthopedic device 100, the knee module 102 is fabricated separately from the lower module 104. The knee module is fabricated by first determining the dimensions, configuration and shape of the portions of the individual's leg positioned above and below the knee. Based upon that information, the lower thigh engaging portion 106 and the calf engaging portion 108 can be designed and fabricated. The lower thigh engaging portion 106 and the calf engaging portion 108 are then connected to one another by means of the metal bars 122. Preferably, the metal bars 122 are molded directly into the laminates forming the lower thigh engaging portion 106 and the calf engaging portion 108 to provide a very strong and rigid connection.

The modular construction of the orthopedic device also lends itself to use with shape sensors and CAD/CAM like technology. It is also within the scope of the invention to use Magnetic Resonance Imaging (MRI) and Kinematic MRI or Cine MRI for assessment, evaluation and prescription. Through the use of such sophisticated technology which measures the shape and joint motion of a limb even under load, the general dimensions, configuration and shape of the appropriate parts of an individual's leg could be determined and then sent to a specialized facility well-suited for fabricating a required module. The present invention encompasses the concept of using such Kinematic MRI-type technology to generate a bracing solution or prescription of an orthopedic device that includes individual connected modules. The information can even be sent by way of computer modem. Through fabrication of the important knee module at a specialized facility that is well versed in the manufacture of such modules and that possesses the necessary trained personnel and manufacturing equipment, it would be possible to manufacture a much higher quality knee module. Once the knee module is completed, the lower module, and possibly other modules, can be attached to the knee module to result in a superior orthopedic device.

The orthosis 100 is also much lighter than other known orthopedic devices. At the same time, the orthosis provides a much more rigid bracing system for resisting torsional forces and other forces to which known orthopedic devices are highly susceptible. Also, the rigid and strong knee module 102 provided by the orthosis 100 significantly reduces, if not eliminates, misalignment of joints and the resulting wear and overstress of the ligaments.

Unlike other known orthopedic devices, the orthosis 100 according to the present invention also provides a substantial total contact fit from the thigh to the calf of the individual. This significantly cuts down on the amount of axial "play" or movement that is typically characteristic of other known orthopedic devices. Of course, it is to be recognized that a small amount of play will be necessary to permit bending and straightening of the knee. The point, however, is that the orthosis 100 provides much more support than known devices of the type depicted in FIG. 1.

The construction of the orthopedic device 100 according to the present invention is designed to axially align the bones of the upper leg and the bones of the lower leg so that the load (i.e., the individual's body weight) is transmitted through the thigh bones and the shin bones and the shin bones of the individual rather than being supported in large part by the orthopedic device itself. By using the bones as partly or fully load supporting members, the bones are less likely to atrophy. Moreover, calcium is maintained in the bones, and, therefore, the bones are less likely to fracture. In addition, since the orthosis 100 does not, in and of itself, support a large part of the load, it is not necessary to extend the orthosis to contact the ischial tuberosity portion of the pelvis. As a result, there is much less chance that the skin and soft tissue in that region will become bruised or sore.

Since the design of the orthosis 100 according to the present invention begins at the knee module and works outwardly (i.e., toward the foot and possibly toward the hip), the orthosis 100 is much better suited for providing the necessary strength and rigidity at the part of the leg that is most susceptible to injury. Moreover, by designing the orthosis 100 in a way that allows for constructing the knee module with sufficient strength and rigidity and closeness of contact with the individual's body, it is possible to avoid problems that may arise as a result of the repeated loading and unloading of the leg during standing and sitting. For example, in the absence of sufficient strength and rigidity in the knee region, knock-kneed individuals find their physical impairment becoming gradually worse as a result of the torsional forces and the repeated loading and unloading to which the knee joint is subjected. The knee module employed in the orthosis 100 according to the present invention is able to provide sufficient strength and side-to-side reinforcement to prevent such problems. Additionally, the close contacting fit of the knee module contributes to this advantageous result.

As noted, the design of the orthopedic device 100 begins with the knee module 102. To determine the necessary characteristics and attributes that the knee module should preferably possess in order to result in an orthopedic device that is optionally suited for performing its intended function, the knee area of the individual should be first analyzed to determine the stresses and forces to which the knee region is subjected. Based on that analysis, the knee module 102 can then be designed with appropriate materials and characteristics for withstanding the stresses and forces to which the knee region is subjected. Thereafter, the lower leg and foot of the individual can be analyzed to determine the stresses and forces to which those parts of the leg are subjected. Thereafter, the lower module can be designed with appropriate materials and characteristics necessary for allowing the lower module to withstand such forces and stresses, and to function as desired.

In the embodiment of the orthosis described above with reference to FIGS. 2–4, the orthosis is constructed of a knee module 102 and a lower module 104. Various changes and variations upon this basic design of constructing an orthopedic device from the knee module and working outwardly are possible. Some of these variations are illustrated in FIGS. 5–7 wherein parts corresponding to those illustrated in the embodiment shown in FIGS. 2–4 are designated with the same reference numerals, but with the addition of a prime designation.

Figure 5:
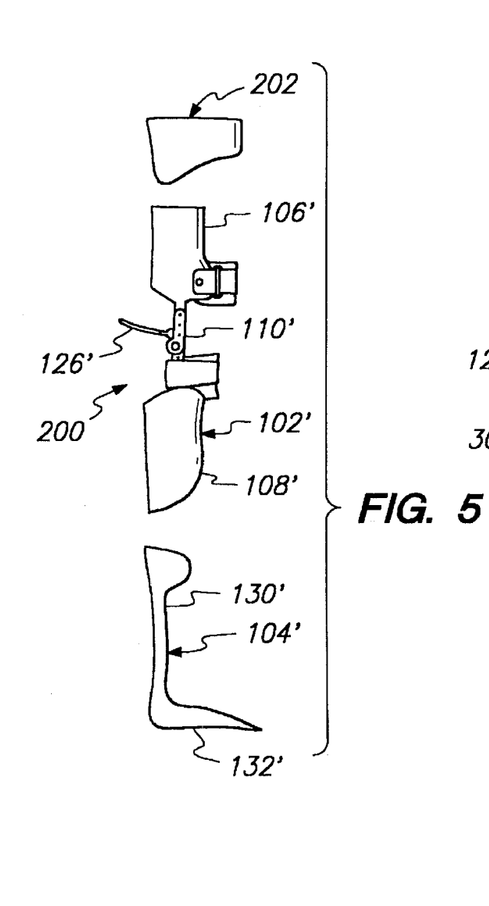
FIG. 5 is an exploded side view of the orthopedic device according to a second embodiment of the present invention.

As shown in FIG. 5, the orthopedic device 200 can include a knee module 102' and a lower module 104' which are connected to one another in the manner described above with respect to the embodiment shown in FIGS. 2–4. The knee module or base module 102' can include the calf engaging portion 108' and the lower thigh engaging portion 106' which are connected to one another by the connecting arrangement 110'. In this embodiment, individual upper module 202 can be separately fabricated for attachment to the knee module 102'. This upper module 202 can be manufactured at a local orthotics facility or elsewhere much in the same manner that the lower module 104' is fabricated. This upper module 202 can then be connected to the upper end of the lower thigh engaging portion 106' in a manner similar to that in which the lower module 104' is connected to the calf engaging portion 108'.

The upper module 202 can actually comprise the upper portion of the lower thigh engaging portion 106 illustrated in the embodiment shown in FIGS. 2–4. This upper module 202 can be fabricated from a material that is suitable for providing the desired characteristics at that portion of the orthopedic device. If desired, the upper module 202 can be designed to encircle not only the upper thigh of the individual but also to act as a connecting member for modules for the hip and pelvic region, if desired. The modular design of the upper module 202 permits the upper module 202 to be specifically adapted to the contour and configuration of an individual's hip and pelvic region so as to provide an orthopedic device that is superior.

Figure 6:
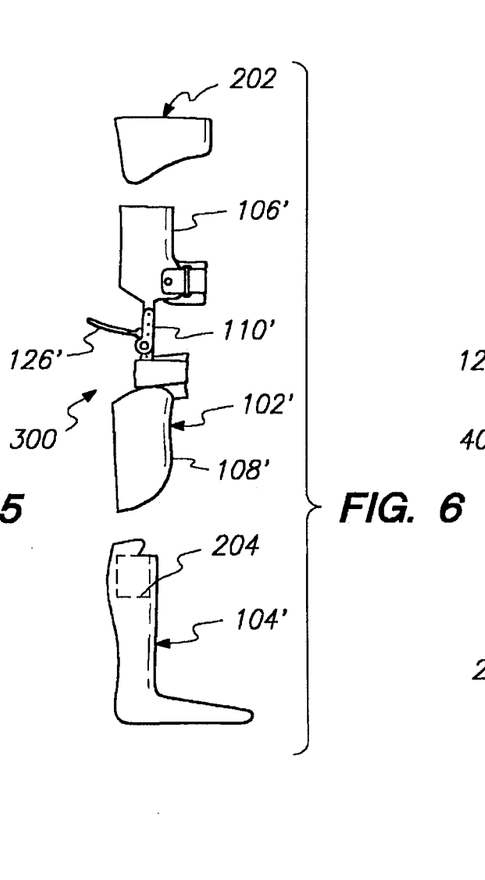
FIG. 6 is an exploded side view of the orthopedic device according to a third embodiment of the present invention.
Figure 7:
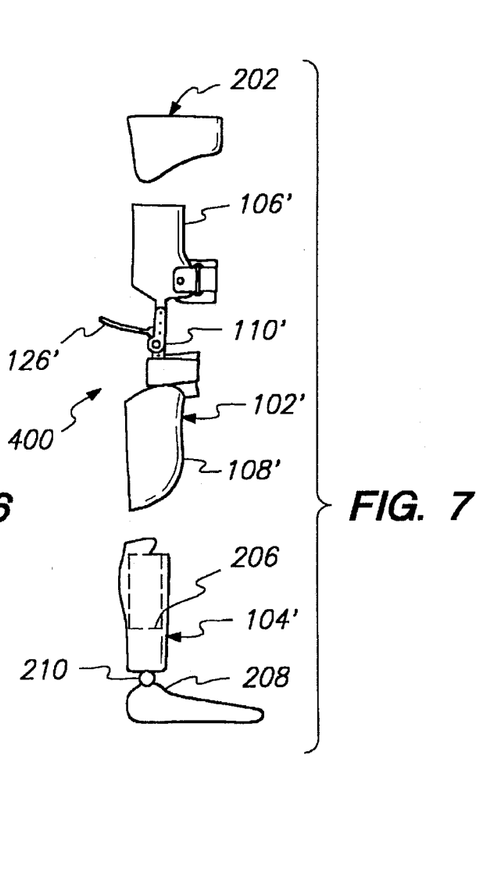
FIG. 7 is an exploded side view of the orthopedic device according to a fourth embodiment of the present invention.

In the embodiment shown in FIG. 6, the orthopedic device 300 includes a knee module or base module 102', a lower module 104', and an upper module 202. The embodiment illustrated in FIG. 6 is particularly suited for aiding the alignment of the thigh bones and shin bones of an individual who has the lower portion of his/her leg amputated. In this regard, the lower module 104' can be designed to have a socket 204 for tightly receiving the remaining portion of the leg. The remainder of the lower module 104' would basically serve as an artificial limb to facilitate the individual's ability to stand and walk. Once again, this modular design encompassed by the present invention permits the multi-faceted type of approach illustrated in FIG. 6 in which the benefits of an orthosis and a prosthesis are combined into a single device.

In the embodiment illustrated in FIG. 7, the orthopedic device 400 includes a knee or base module 102', a lower module 104' and an upper module 202. This particular embodiment of the device is designed for use by an individual whose leg has been amputated at or near the ankle. In this regard, the lower module 104' is provided with a socket 206 for tightly receiving the remaining portion of the lower leg. The bottom portion of the lower module 104' then serves as an ankle/foot prosthetic device. This bottom section can include an artificial foot 208 and an artificial ankle joint 210 such as those known in the industry.

Other related variations on the embodiments shown in FIGS. 6 and 7 are also possible. For example, the foot portion of the prosthetic lower modules 104' shown in FIGS. 6 and 7 could be replaced with other types of prosthetic devices currently on the market, such as the Carbon Copy II Energy-Storing Foot offered for sale by the Ohio Willow Wood Company in Mr. Sterling, Ohio, or the Modular II™ Flex-Foot® and the Flex-Walk™ sold by Flex-Foot® Inc. in Laguna Hills, Calif.

Additionally, as noted above, each of the designs could be provided with an upper module that encompasses not only the upper thigh but also the hip and pelvic regions. Such an upper module might employ characteristics similar to those utilized in the Newport Hip Orthosis sold by Orthomerica™ Products, Inc. in Newport Beach, Calif.

The orthopedic device according to the present invention has been described above in the context of an aid for aligning the upper and lower parts of an individual's leg to facilitate standing or walking, which would include protecting the knee structures of an injured knee. It is to be understood, however, that the benefits associated with designing an orthopedic device by initially beginning at an intermediate part of the device that is important to the overall design and functioning of the device and then working outwardly is applicable to other types of orthopedic devices. Similarly, the modular approach to designing an orthopedic appliance can be used in other areas of the body as well.

For example, it may be useful to employ a similar methodology in the design and fabrication of a brace for the arm and hand. In this context, the design of the device would begin at the elbow region, and an elbow module would be fabricated as the basic "building block". The elbow module could be designed and fabricated to take into account the particular characteristics and requirements at the elbow joint. Another module, for example a wrist/hand module, could then be attached to the elbow module. This wrist/hand module could also be designed to possess the characteristics necessary to achieve the objectives desired.

The principles, preferred embodiments and modes of operation of the present invention have been described in the foregoing specification. However, the invention which is intended to be protected is not to be construed as being limited to the particular embodiments disclosed. Further, the embodiments described herein are to be regarded as being illustrative rather than restrictive. Variations, changes and equivalents may be made by others without departing from the spirit of the present invention. Accordingly, it is expressly intended that all such variations, changes and equivalents which fall within the spirit and scope of the present invention as defined in the claims be embraced thereby.

What is claimed is:

1. A method of manufacturing a body-worn orthopedic device for use by a physically impaired individual to aid in alignment of the individual's tibia and femur, comprising the steps of:

fabricating a knee module for being positioned on an individual's knee as well as portions of the individual's leg located above and below the knee, said step of fabricating the knee module including:

determining the dimensions and configuration of the individual's lower thigh;

fabricating a lower thigh engaging portion to closely contact the individual's lower thigh based upon the determined dimensions and configuration of the individual's lower thigh;

determining the dimensions and configuration of the individual's calf;

fabricating a calf engaging portion to closely contact the individual's calf based upon the determined dimensions and configuration of the individual's calf;

connecting the lower thigh engaging portion to the calf engaging portion by a hinge means that permits movement of the calf engaging portion relative to the lower thigh engaging portion;

providing said hinge means with locking means for permitting said calf engaging portion to be locked in a substantially axially aligned position with respect to said lower thigh engaging portion; and fabricating a lower module for engaging the individual's lower leg and foot, and connecting the lower module to the calf engaging portion of the knee module wherein said step of fabricating said lower module includes fabricating said lower module from a composition of material that is different from the composition of material from which said lower thigh engaging portion and said calf engaging portion are fabricated.

2. The method according to claim 1, wherein said step of fabricating said lower module includes fabricating said lower module to be generally L-shaped with a portion adapted to engage the back part of the lower leg of the individual and a portion adapted to be positioned under the individual's foot.

3. The method according to claim 1, including the steps of fabricating an upper module for engaging the individual's upper thigh, and connecting the upper module to the lower thigh engaging portion of the knee module.

4. The method according to claim 1, wherein said step of determining the dimensions and configuration of the individual's lower thigh and calf is performed through use of Computer-Aided Design, Computer-Aided Machining type technology, the dimensions and configuration obtained through use of Computer-Aided Design, Computer-Aided Machining type technology being used to fabricate the knee module at a first facility, and said lower module being fabricated at a second facility.

5. A method of manufacturing a body-worn orthopedic device for use by a physically impaired individual to aid in alignment of the individual's tibia and femur, comprising the steps of:

fabricating a knee module for being positioned on an individual's knee as well as portions of the individual's leg located above and below the knee, said step of fabricating the knee module including:

determining the dimensions and configuration of the individual's lower thigh;

fabricating a lower thigh engaging portion to closely contact the individual's lower thigh based upon the determined dimensions and configuration of the individual's lower thigh;

determining the dimensions and configuration of the individual's calf;

fabricating a calf engaging portion to closely contact the individual's calf based upon the determined dimensions and configuration of the individual's calf wherein the steps of fabricating the lower thigh engaging portion and the calf engaging portion include fabricating the lower thigh engaging portion and the calf engaging portion from a composition of reinforcing fibers and plastic, and the step of fabricating the lower module includes fabricating the lower module from a composition of plastic that is devoid of reinforcing fibers so that said lower module is more flexible than said lower thigh engaging portion and said calf engaging portion and so that said calf engaging portion and said lower thigh engaging portion are more rigid than said lower module;

connecting the lower thigh engaging portion to the calf engaging portion by a hinge means that permits movement of the calf engaging portion relative to the lower thigh engaging portion; and providing said hinge means with locking means for permitting said calf engaging portion to be locked in a substantially axially aligned position with respect to said lower thigh engaging portion; and fabricating a lower module for engaging the individual's lower leg and foot, and connecting the lower module to the calf engaging portion of the knee module.

6. The method according to claim 5, wherein said step of determining the dimensions and configuration of the individual's lower thigh and calf is performed through use of Computer-Aided Design, Computer-Aided Machining type technology, the dimensions and configuration obtained through use of Computer-Aided Design, Computer-Aided Machining type technology being used to fabricate the knee module at a first facility, and said lower module being fabricated at a second facility.

7. A method of designing a body-worn orthopedic device for use by a physically impaired individual to aid in the functioning of a body part that includes a joint, said device including a base module and another module connected to the base module, the method comprising the steps of:

first analyzing the joint of the individual to determine the stresses and forces to which the joint is subjected;

designing a base module to be worn by the individual in the area of the joint, said step of designing the base module including designing a first section for closely contacting a portion of the individual's body on one side of the joint, a second section for closely contacting a portion of the individual's body on an opposite side of the joint and a connecting section for connecting the first and second sections and for permitting movement of the joint, said first section, said second section and said connecting section being designed to result in a base module that possesses characteristics necessary for withstanding the stresses and forces to which the joint is subjected;

analyzing the portion of the body part of the individual remote from the joint to determine the stresses and forces to which said portion of the body part is subjected; and designing a lower module that is to be connected to closely contact said portion of the body part, said lower module being designed to result in a lower module that possesses characteristics necessary for withstanding the stresses and forces to which said portion of the body part is subjected wherein said first section and said second section are designed to be fabricated of a composition of material that is different from the composition of material from which the lower module is to be fabricated.

8. The method according to claim 7, wherein said step of analyzing the joint of the individual includes analyzing the knee joint of the individual, and wherein said step of analyzing the portion of the body part remote from the joint includes analyzing the lower leg and foot of the individual.

9. The method according to claim 7, wherein said step of designing the connecting section includes designing the connecting section to include locking means for locking the second section relative to the first section in an axially aligned manner.

10. The method according to claim 7, wherein said step of analyzing includes scanning of the body part of the individual and generating a bracing solution for said body part.

* * * * *